United States Patent
Yada et al.

(10) Patent No.: US 7,388,108 B2
(45) Date of Patent: Jun. 17, 2008

(54) OXIDATION REACTOR, PROCESS FOR PRODUCING (METH)ACRYLIC ACIDS, AND METHOD FOR ANALYZING EASILY-POLYMERIZABLE COMPOUNDS

(75) Inventors: Shuhei Yada, Mie-ken (JP); Yasushi Ogawa, Mie-ken (JP); Yoshiro Suzuki, Mie-ken (JP); Hirochika Hosaka, Mie-ken (JP); Yasuhiko Samura, Mie-ken (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 11/586,691

(22) Filed: Oct. 26, 2006

(65) Prior Publication Data

US 2007/0043239 A1    Feb. 22, 2007

Related U.S. Application Data

(60) Division of application No. 10/808,546, filed on Mar. 25, 2004, which is a continuation of application No. PCT/JP02/12654, filed on Dec. 3, 2002.

(30) Foreign Application Priority Data

| Dec. 6, 2001 | (JP) | ............................. 2001-372954 |
| Dec. 6, 2001 | (JP) | ............................. 2001-372955 |
| Dec. 27, 2001 | (JP) | ............................. 2001-396344 |

(51) Int. Cl.
*C07C 51/16* (2006.01)
*G01N 35/08* (2006.01)

(52) U.S. Cl. ........................................ 562/546; 436/52

(58) Field of Classification Search ..................... None
See application file for complete search history.

(56) References Cited

U.S. PATENT DOCUMENTS 3,883,588 A * 5/1975 Schlaefer .................... 562/546

6,355,150 B1   3/2002 Savin-Poncet et al.

FOREIGN PATENT DOCUMENTS

| JP | 53-21140 U | 2/1978 |
| JP | 53-94940 U | 8/1978 |
| JP | 54-42194 | 4/1979 |
| JP | 54-48690 | 4/1979 |
| JP | 56-95330 U | 7/1981 |
| JP | 58-147646 | 9/1983 |
| JP | 60-31663 | 3/1985 |
| JP | 02-052236 | 2/1990 |
| JP | 05-256833 | 10/1993 |
| JP | 6-6295 U | 1/1994 |
| JP | 08-259488 | 10/1996 |
| JP | 9-323950 A | 12/1997 |
| JP | 2001-235404 | 8/2001 |
| WO | WO 99/58950 A1 | 11/1999 |

* cited by examiner

*Primary Examiner*—Paul A Zucker
(74) *Attorney, Agent, or Firm*—Nixon & Vanderhye P.C.

(57) ABSTRACT

An oxidation reactor includes a reactor body, a manhole nozzle projecting from the reactor body, and a partition plate separating an inside of the manhole nozzle and an inside of the reactor body from each other. In an oxidation reactor including the reactor body and a nozzle projecting from the reactor body, there is provided a means for feeding an inert gas into the nozzle. In a process for producing (meth)acrylic acids by subjecting propane, propylene or isobutylene to catalytic gas-phase oxidation reaction in an oxidation reactor for producing (meth)acrolein or (meth)acrylic acid, the above oxidation reactor is used as the oxidation reactor. In a method for analyzing an easily-polymerizable compound by introducing a gas containing the easily-polymerizable compound into an analyzing apparatus through a sampling tube, a double tube is used as the sampling tube, and a heating medium is fed into an outer tube of the double tube. According to these methods, the oxidation reaction can be stably conducted, and the reaction product gas can be prevented from being condensed and polymerized in the sampling tube, so that an on-line analysis can be performed at a high accuracy for a long period of time.

4 Claims, 4 Drawing Sheets

PROCESS FOR PRODUCTION OF ACRYLIC ACID
(PROPYLENE TWO-STAGE OXIDATION METHOD)

OXIDATION REACTOR, PROCESS FOR PRODUCING (METH)ACRYLIC ACIDS, AND METHOD FOR ANALYZING EASILY-POLYMERIZABLE COMPOUNDS

This application is a division of application Ser. No. 10/808,546, filed Mar. 25, 2004, which in turn is a continuation of PCT International Application No. PCT/JP02/12654 filed in Japanese on Dec. 3, 2002, which designated the U.S.; PCT/JP02/12654 claims priority to JP Application No. 2001-32954 filed Dec. 6, 2001, JP Application No. 2001-372955 filed Dec. 6, 2001 and JP Application No. 2001-396344 filed Dec. 27, 2001, the entire content of each of which is hereby incorporated by reference in this application.

TECHNICAL FIELD

The present invention relates to an oxidation reactor, a process for producing (meth)acrylic acids using the oxidation reactor, and a method for analyzing easily-polymerizable compounds such as (meth)acrylic acids. In the present invention, the (meth)acrylic acids include (meth)acrolein or (meth)acrylic acid in which the (meth)acrolein means acrolein or methacrolein, and the (meth)acrylic acid means acrylic acid and methacrylic acid.

BACKGROUND ARTS

As well known in the art, acrylic acid is produced from propylene by gas-phase oxidation method. This method for producing acrylic acid by oxidizing propylene, includes a first stage reaction for oxidizing propylene into acrolein and a second stage reaction for oxidizing the acrolein into acrylic acid which are conducted under different oxidation conditions from each other. Therefore, as the above method, there are known a two-stage oxidation process in which the respective reactions are performed using different kinds of catalysts or separate reactors, and a one-stage oxidation process using a single reactor filled with plural kinds of catalysts.

FIG. 1 shows an example of a flow chart for producing acrylic acid by the two-stage oxidation process. In the process shown in FIG. 1, propylene, steam and air are fed through the first reactor and the second reactor filled with molybdenum-based catalysts, etc., and subjected to two stage oxidation reactions therein to obtain an acrylic acid-containing gas. The thus obtained acrylic acid-containing gas is fed to a condensation column (quench column) where the gas is contacted with water to prepare an aqueous acrylic acid solution. The aqueous acrylic acid solution is fed to an extraction column where acrylic acid is extracted with an appropriate extractant added thereto, and the obtained extract solution is then fed to a solvent separation column to separate the extractant therefrom. Next, the obtained solution is fed to an acetic acid separation column where acetic acid is removed therefrom to prepare crude acrylic acid. The thus prepared crude acrylic acid is then fed to a rectifying column to separate by-products from the crude acrylic acid, thereby obtaining purified acrylic acid.

Meanwhile, in recent years, in order to recover acrylic acid from the aqueous acrylic acid solution, instead of the above solvent extraction method using the extractant, there has been used an azeotropic separation method in which the aqueous acrylic acid solution is distilled using water and an azeotropic solvent to distil off an azeotropic mixture of water and the azeotropic solvent from a top of an azeotropic separation column and recover acrylic acid from a bottom thereof.

Methacrylic acid is produced by gas-phase oxidation reaction of isobutylene. In the case where methacrylic acid is produced by two-stage oxidation method, isobutylene is oxidized into methacrylic acid through methacrolein.

The gas-phase oxidation reaction of propylene or isobutylene is conducted within an oxidation reactor filled with an oxidation catalyst. The oxidation reactor includes a container-like reactor body, and a manhole nozzle projecting from the reactor body. The manhole nozzle is closed by a lid fitted to a tip end thereof upon normal operation of the reactor. The lid is opened upon inspection of an inside of the reactor, replacement of the catalyst or the like.

Also, although not shown in the figure, in order to fit various sensors or gauges, etc., to the reactor, the reactor body may be frequently provided with measuring device-mounting nozzles to which the sensors or gauges may be fitted. Further, the reactor may also be frequently provided with a small diameter nozzle serving as an opening for inspection of an inside of the reactor.

When viewed from the inside of the reactor body, portions where the above respective nozzles projecting from the reactor body are provided, form recesses partially depressed from an inner surface of the reactor. These recesses tend to cause undesirable retention of a reaction gas. For this reason, in the above conventional reactors, an easily-oxidizable substance gas such as (meth)acrolein tends to be retained inside of the respective nozzles and automatically oxidized therein, thereby causing unstable oxidation reaction of the gas.

Since these nozzles projecting from the reactor body tend to be cooled by outside air, etc., the easily-polymerizable substances such as (meth) acrolein and (meth)acrylic acid may be liquefied and retained therein to produce polymers thereof. As a result, the nozzles tend to be clogged, so that it may become extremely difficult to open the nozzles and manholes upon terminating operation of the reactor, etc.

On the other hand, as a method of sampling and analyzing a gas containing the above easily-polymerizable compound, there are known a method using a reaction product gas sampling tube, a gas-liquid separation method, a sampling container method, a sensor method or the like.

Among these methods, the method using a reaction product gas sampling tube is industrially advantageous from viewpoints of simple facilities and low costs. As the reaction product gas sampling tube, there may be mainly used a stainless steel sampling tube around which an electric heater or a steam trace is fitted.

However, the stainless steel sampling tube around which the electric heater is fitted, has the following problems. That is, although portions at which thermocouples are provided for temperature control are maintained at a set temperature, other portions of the sampling tube tend to undergo undesirable temperature distribution depending upon winding conditions of the electric heater or heat-retention conditions. As a result, easily-condensable substances tend to be condensed at the low-temperature portions, so that an analysis accuracy thereof tends to be deteriorated. Further, acrylic acid whose polymerization is inhibited in a gas state but is promoted in a liquid state, tends to condensed and polymerized at the low-temperature portions formed due to the temperature distribution. If the operation of the sampling tube is continued, the sampling tube tends to suffer from clogging, resulting in failed analysis. In particular, since a longer sampling tube undergoes a larger temperature distribution, the use of such a longer sampling tube tends to further deteriorate the analysis accuracy, and promote clogging thereof. In addition, at the time other than the analysis, the reaction production gas is retained within the sampling tube, so that the easily-condensable and easily-polymerizable substances tend to be condensed, polymerized and adhered to an inside of the sampling tube, also resulting in problems such as clogging thereof.

In the case where the steam trace is wound around the stainless steel sampling pipe, it may be difficult to uniformly wind the steam trace around the thin sampling tube, resulting in occurrence of temperature distribution in the sampling tube, especially formation of the low-temperature portions therein. Therefore, the latter method using the steam trace has similar problems to those of the former method using the electric heater, such as deteriorated analysis accuracy, tendency of causing clogging in the sampling tube and difficulty in long-term continuous operation thereof. Thus, both of the above methods are unsatisfactory from industrial viewpoints.

In Japanese Patent Application Laid-open (KOKAI) No. 8-259488, to solve the above problems, there has been proposed the sampling tube whose inner wall is made of a fluorine-based resin. The sampling tube whose inner wall is made of a fluorine-based resin is more effective to prevent a condensate of the easily-condensable substances from adhering to an inside of the sampling tube as compared to the stainless steel sampling tube. However, the sampling tube whose inner wall is made of a fluorine-based resin is still unsolved as to the problem concerning temperature distribution, resulting in low analysis accuracy. In addition, the sampling tube whose inner wall is made of a fluorine-based resin is also still unsolved as to such a problem that at the time other than the analysis, the reaction production gas is retained within the sampling tube, so that the easily-condensable and easily-polymerizable substances tend to be condensed, polymerized and adhered to an inside of the sampling tube, thereby causing the clogging of the sampling tube.

An object of the present invention is to provide an oxidation reactor that is free from recesses formed on an inner surface of a reactor body thereof so as to conduct a stable oxidation reaction therein, as well as a process for producing (meth)acrylic acids using the oxidation reactor.

Another object of the present invention is to provide an oxidation reactor that is free from undesirable retention of gas at recesses formed on an inner surface of a reactor body thereof so as to conduct a stable oxidation reaction therein, as well as a process for producing (meth)acrylic acids using such an oxidation reactor.

A further object of the present invention is to provide an on-line analysis process for analyzing an easily-polymerizable compound by introducing a gas containing the easily-polymerizable compound into an analyzing apparatus through a reaction production gas sampling tube in which the reaction production gas is prevented from being condensed and polymerized in the sampling tube, thereby ensuring a long-term stable analysis with a high efficiency.

DISCLOSURE OF THE INVENTION

In a first aspect of the present invention, there is provided an oxidation reactor comprising a reactor body and a manhole nozzle projecting from the reactor body, in which a partition plate is provided to separate an inside of the manhole nozzle and an inside of the reactor body from each other. In such an oxidation reactor according to the first aspect of the present invention, since the inside of the manhole nozzle is separated from the inside of the reactor body by the partition plate, the inner surface of the reactor body is free from recesses depressed therefrom when view from the inside of the reactor body. Therefore, the reaction gas is prevented from being retained therein, so that automatic oxidation of (meth)acrolein and formation of polymers of (meth)acrolein or (meth)acrylic acid can be inhibited. In the oxidation reactor, the manhole nozzle may be purged with an inert gas by feeding the inert gas thereinto. Also, the inside of the manhole nozzle may be kept under a positive pressure by the inert gas.

In a second aspect of the present invention, there is provided a process for producing (meth)acrylic acids by subjecting propane, propylene or isobutylene to catalytic gas-phase oxidation reaction in an oxidation reactor for producing. (meth)acrolein or (meth)acrylic acid, wherein the oxidation reactor as defined in the above first aspect is used as the oxidation reactor.

In a third aspect of the present invention, there is provided an oxidation reactor comprising a reactor body and a nozzle projecting from the reactor body, in which the nozzle is provided therein with a means for feeding an inert gas thereinto. In the oxidation reactor according to the third aspect of the present invention, since the inside of the nozzle is purged with an inert gas by feeding the inert gas thereinto, the reaction gas is prevented from being retained in the nozzle recessed from an inner surface of the reactor body when viewed from the inside of the reactor body, so that automatic oxidation of (meth)acrolein and formation of polymers of (meth)acrolein or (meth)acrylic acid are inhibited.

In a fourth aspect of the present invention, there is provided a process for producing (meth)acrylic acids by subjecting propane, propylene or isobutylene to catalytic gas-phase oxidation reaction for producing (meth)acrolein or (meth)acrylic acid, wherein the oxidation reactor as defined in the above third aspect is used as the oxidation reactor.

In a fifth aspect of the present invention, there is provided a method for analyzing an easily-polymerizable compound by introducing a gas containing the easily polymerizable compound into an analyzing apparatus through a sampling tube, wherein the sampling tube is a double tube, and a heating medium is fed into an outer tube of the sampling tube.

Next, the process of the present invention is described by referring to the accompanying drawings.

Figure 1:
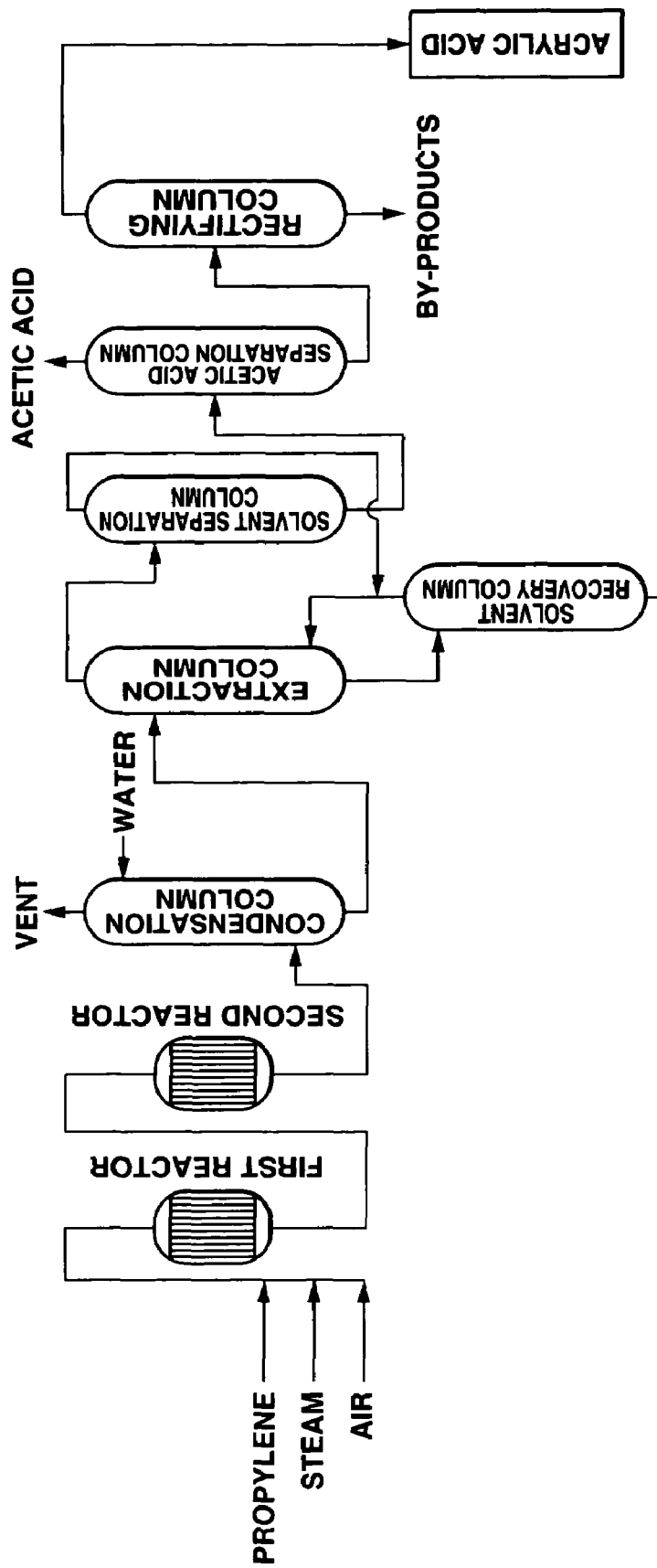
FIGS. 1 and 2 are flow charts showing a process for producing acrylic acid.
Figure 2:
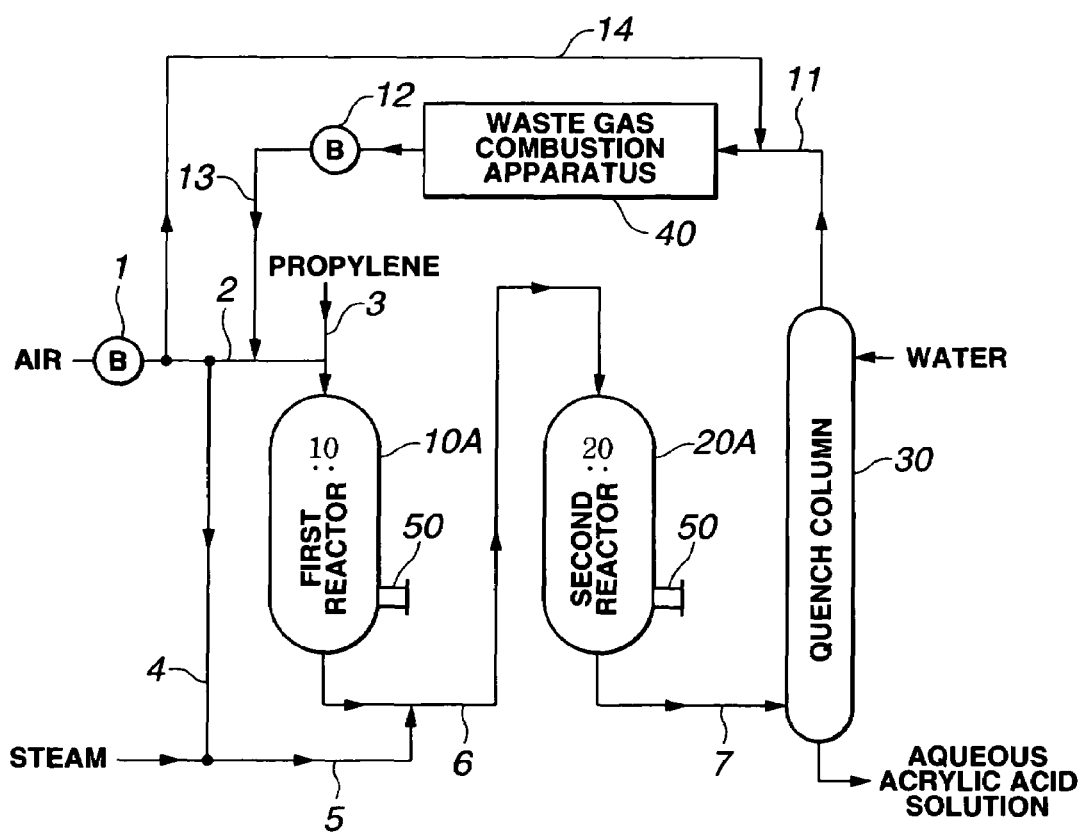

As shown in FIG. 2, first reactor 10 is supplied with air through blower 1 and line 2, with a combustion waste gas through line 13, and with propylene through line 3.

The first reactor 10 is filled with an oxidation catalyst such as molybdenum-based catalysts to conduct an oxidation reaction for production of acrolein (meanwhile, details of the catalyst are explained later). An acrolein-containing gas discharged from first reactor 10 through line 6 is mixed with steam and air supplied through line 5, and the resultant mixed gas is introduced into second reactor 20. The supply of the steam and air through line 5 may be sometimes omitted according to composition of the gas supplied to first reactor 10. The second reactor 20 is also filled with an oxidation catalyst such as molybdenum-based catalysts to oxidize acrolein into acrylic acid. The resultant acrylic acid gas is introduced into a quench column (collecting column) 30 through line 7 where the acrylic acid gas is contacted with water to prepare an aqueous acrylic acid solution. A gas component containing unreacted propylene, etc., is removed from a top of quench column 30, and mixed with air supplied through line. 14. The obtained mixed gas is fed to waste gas combustion apparatus 40 where the mixed gas is burned. The resultant combustion gas is fed to first reactor 10 through blower 12 and line 13. As waste gas combustion apparatus 40, there may be used an incineration-type apparatus using a combustion oil, a catalyst oxidation combustion-type apparatus using a noble metal catalyst, or various other apparatuses.

The respective reactors 10 and 20 are provided with a manhole nozzle 50 for inspection of an inside of the reactors or replacement of the catalyst. The manhole nozzle 50 is of a generally cylindrical shape, and projects outwardly from reactor body 10A or 20A of reactor 10 or 20. The manhole nozzle 50 is formed at a projecting end thereof with a flange to which lid 55 is mounted by bolts, etc.

Figure 5:
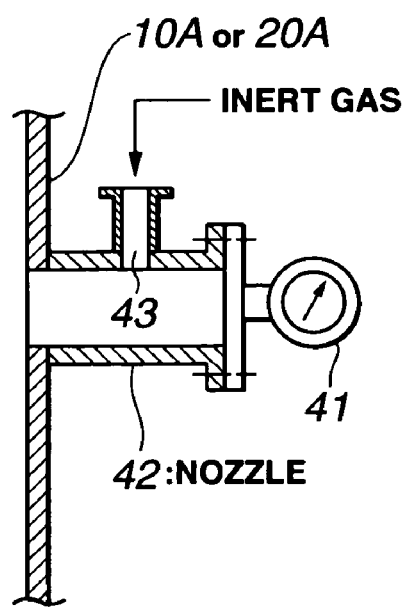
FIG. 5 is a sectional view showing portions near a measuring device-mounting nozzle of a reactor.

In addition, although not shown in FIG. 2, in order to mount sensor or gauge 41, etc., to the reactor, measuring device-mounting nozzle 42 as shown in FIG. 5 is provided so as to project from reactor body 10A or 20A. The sensor or gauge 41 is mounted to measuring device-mounting nozzle 42.

In the oxidation reactor according to the first aspect of the present invention which includes the reactor body and the manhole nozzle projecting from the reactor body, a partition plate is provided to separate the inside of the manhole nozzle and the inside of the reactor body from each other.

Figure 3:
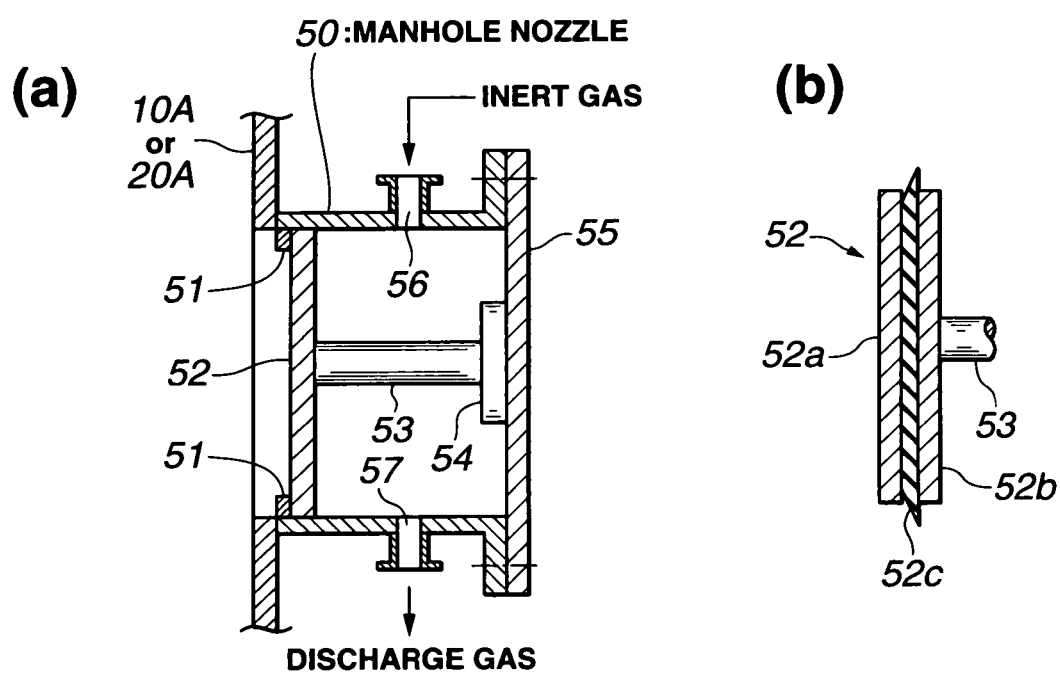
FIGS. 3 and 4 are sectional views showing portions near a manhole nozzle of a reactor.

That is, as shown in FIG. 3(*a*), manhole nozzle 50 is provided, at a reactor body-side end portion thereof, with stopper 51 projecting inwardly from an inner surface thereof, and partition plate 52 is arranged in manhole nozzle 50 so as to abut against stopper 51.

In this embodiment, rod 53 projects rearwardly (outwardly) from partition plate 52, and receiving plate 54 is securely attached to a tip end of rod 53 such that lid 55 abuts against receiving plate 54, thereby allowing partition plate 52 to be fixed in abutting contact with stopper 51.

The partition plate 52 has, as shown in FIG. 3(*b*), such a structure that seal packing 52*c* is interposed between a pair of circular plates 52*a* and 52*b*. The sheet-like seal packing 52*c* projects from an outer periphery of plates 52*a* and 52*b*, and is air-tightly contacted with an inner peripheral surface of manhole nozzle 50.

The partition plate 52 serves for isolating the inside of manhole nozzle 50 from the inside of reactor body 10A or 20A.

In this embodiment, in order to purge the inside of manhole nozzle 50 with an inert gas, manhole nozzle 50 is provided with feed port 56 and discharge port 57 for the inert gas. The purging with the inert gas allows a reaction gas leaked through a periphery of partition plate 50 into the manhole nozzle to be discharged out of manhole nozzle 50. Further, when the pressure of the inert gas is adjusted to higher than an inside pressure of the reactor, the reaction gas is effectively prevented from entering into the manhole nozzle through the periphery of partition plate 52. As the inert gas, there may be preferably used a nitrogen gas, a carbon dioxide gas, etc. Also, as the inert gas, there may be used a combustion waste gas discharged from waste gas combustion apparatus 40. When the combustion waste gas discharged from waste gas combustion apparatus, 40 is used as the inert gas, waste gas combustion apparatus 40 may be preferably a catalytic oxidation combustion type apparatus using a noble metal catalyst. The waste gas combustion apparatus 40 of a catalytic oxidation combustion type can discharge a combustion waste gas having a stable oxygen concentration, so that the composition of an atmosphere inside of manhole nozzle 50 is surely controlled out of an explosion limit.

In the thus constructed oxidation reactor 10, 20, since the inside of manhole nozzle 50 is closed by partition plate 52, there exist no deep recesses depressed from an inner surface of reactor body 10A, 20A of the oxidation reactor. Therefore, the reaction gas is inhibited from being locally retained in the reactor body, thereby preventing automatic oxidation of acrolein.

In particular, in this embodiment, since the inside of manhole nozzle 50 is purged with the inert gas, accumulation of the reaction gas within manhole nozzle 50 is also prevented.

In order to prevent the gas within manhole nozzle 50 from being condensed, the manhole nozzle 50 may be provided with, for example, a heating means and/or a heat-retaining means using steam having a temperature of about 200° C. Further, the oxidation reactor 10, 20 may be provided with a sampling tube for sampling an easily-polymerizable compound-containing gas (as described in detail hereinafter).

The oxidation reactor according to the third aspect of the present invention includes a reactor body, a nozzle projecting from the reactor body, and a means for feeding an inert gas into the nozzle.

Figure 4:
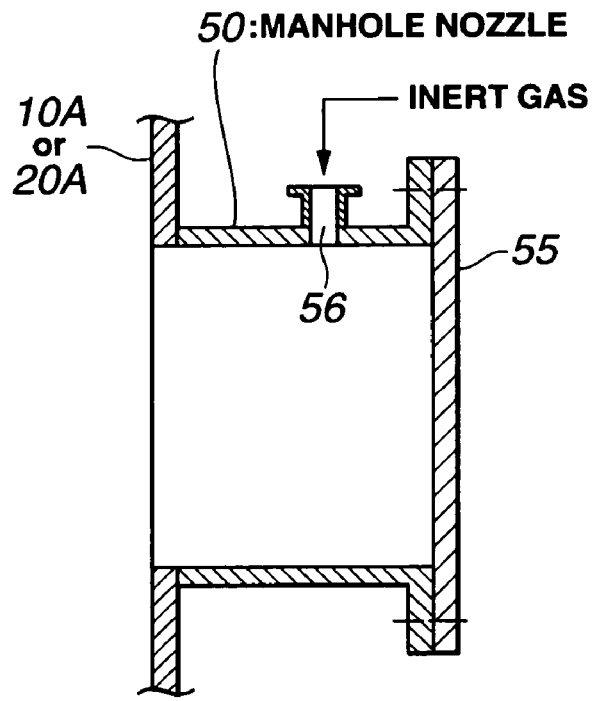

That is, as shown in FIG. 4, the manhole nozzle 50 is provided with feed port 56 for introducing an inert gas thereinto. Further, as shown in FIG. 5, the measuring device-mounting nozzle 42 may also be provided with feed port 43 for introducing the inert gas thereinto. In both the nozzles, the inert gas introduced through these feed ports is fed into the reactor body to purge the inside thereof. Meanwhile, the measuring device-mounting nozzle 42 may be fitted with meters, relief valves or the like. In addition, although not shown in the figures, there may also be provided other nozzles such as sampling nozzle and rupture disk-fitting nozzle.

As the inert gas fed to measuring device-mounting nozzle 42 and manhole nozzle 50, there may be used the same inert gases as described above. When the combustion waste gas having a stable oxygen concentration is used, the composition of an atmosphere inside of measuring device-mounting nozzle 42 and manhole nozzle 50 is surely controlled out of an explosion limit.

In the thus constructed oxidation reactor 10, 20, since the inert gas is directly introduced into measuring device-mounting nozzle 42 and manhole nozzle 50 which are recessed from an inner surface thereof when viewed from the inside of reactor body, the reaction gas can be inhibited from being retained inside of measuring device-mounting nozzle 42 and manhole nozzle 50, thereby preventing automatic oxidation of acrolein as well as deposition of polymers.

In order to prevent the gases within measuring device-mounting nozzle 42 and manhole nozzle 50 from being condensed, the measuring device-mounting nozzle 42 and manhole nozzle 50 may be provided with, for example, a heating means and/or a heat-retaining means using steam having a temperature of about 200° C.

Meanwhile, the process shown in FIG. 2 is a combustion waste gas recycling process in which propylene, air and steam are mixed with each other and fed into a first reactor to oxidize the mixed gas into mainly acrolein and acrylic acid; the reaction gas from the first reactor is fed to a second reactor to obtain a reaction production gas containing acrylic acid as a main component; the reaction production gas is then introduced into a quench column to collect and recover acrylic acid in the form of an aqueous solution thereof; and a whole amount of waste gas from the quench column is burned by a combustion apparatus and recycled to an inlet of the first reactor. As other processes, there may be used one-pass process, unreacted propylene recycling process, etc.

The one-pass process is such a process in which the outlet gas from the second reactor is not recycled, more specifically, propylene, air and steam are mixed with each other and fed to the first reactor to convert the mixed gas into mainly acrolein and acrylic acid, and the outlet gas from the first reactor is fed to the second reactor without separation of reaction products obtained in the first reactor therefrom. At this time, in general, there may also be used such a process in which air and steam required for the reaction in the second reactor are added to the outlet gas from the first reactor, and the resultant mixed gas is fed to the second reactor.

The unreacted propylene recycling process is such a process in which an acrylic acid-containing reaction product gas obtained at an outlet of the second reactor is introduced into an acrylic acid-collecting apparatus to collect and recover the acrylic acid in the form of an acrylic acid solution, and a part of a waste gas containing unreacted propylene is recycled from the collecting apparatus to an inlet gas of the first reactor.

The process for producing (meth)acrylic acids according to the present invention is characterized in that in a process for producing (meth)acrylic acids by subjecting propane, propylene or isobutylene to catalytic gas-phase oxidation reaction in an oxidation reactor for producing (meth)acrolein or (meth)acrylic acid, the oxidation reactor previously described is used as the oxidation reactor.

In the above catalytic gas-phase oxidation reaction, as the Mo—Bi-based composite oxide catalysts used in the front-stage reaction for producing mainly acrolein (reaction for converting olefins into unsaturated aldehydes or unsaturated acids), there may be used compounds represented by the following general formula (1):

$$Mo_aW_bBi_cFe_dA_eB_fC_gD_hE_iO_x \qquad (1)$$

wherein Mo is molybdenum; W is tungsten; Bi is bismuth; Fe is iron; A is at least one element selected from the group consisting of nickel and cobalt; B is at least one element selected from the group consisting of sodium, potassium, rubidium, cesium and thallium; C is at least one element selected from the group consisting of alkali earth metals; D is at least one element selected from the group consisting of phosphorus, tellurium, antimony, tin, cerium, lead, niobium, manganese, arsenic, boron and zinc; E is at least one element selected from the group consisting of silicon, aluminum, titanium and zirconium; O is oxygen; and a, b, c, d, e, f, g, h, i and x are atomic ratios of Mo, W, Bi, Fe, A, B, C, D, E and O, respectively, with the proviso that when a is 12 (a=12), $0 \leq b \leq 10$, $0 \leq c \leq 10$ (preferably $0.1 \leq c \leq 10$), $0 \leq d \leq 10$ (preferably $0.1 \leq d \leq 10$), $2 \leq e \leq 15$, $0 \leq f \leq 10$ (preferably $0.001 \leq f \leq 10$), $0 \leq g \leq 10$, $0 \leq h \leq 4$, $0 \leq i \leq 30$, and x is a value determined by oxidation degrees of the respective elements.

In the above catalytic gas-phase oxidation reaction, as the Mo—V-based composite oxide catalysts used in the rear-stage reaction for producing acrylic acid by oxidizing acrolein (reaction for converting unsaturated aldehydes into unsaturated acids), there may be used compounds represented by the following general formula (2):

$$Mo_aV_bW_cCu_dX_eY_fO_g \qquad (2)$$

wherein Mo is molybdenum; V is vanadium; W is tungsten; Cu is copper; X is at least one element selected from the group consisting of Mg, Ca, Sr and Ba; Y is at least one element selected from the group consisting of Ti, Zr, Ce, Cr, Mn, Fe, Co, Ni, Zn, Nb, Sn, Sb, Pb and Bi; O is oxygen; and a, b, c, d, e, f and g are atomic ratios of Mo, V, W, Cu, X, Y and O, respectively, with the proviso that when a is 12 (a=12), $2 \leq b \leq 14$, $0 \leq c \leq 12$, $0 \leq d \leq 6$, $0 \leq e \leq 3$, $0 \leq f \leq 3$, and g is a value determined by oxidation degrees of the respective elements.

The catalyst used in the present invention may be in the form of a molded catalyst produced by an extrusion-molding method or a tablet-forming method, or may be in the form of a supported catalyst obtained by supporting the composite oxide as a catalyst component on an inert carrier such as silicon carbide, alumina, zirconium oxide and titanium oxide. The shape of the catalyst used in the present invention is not particularly restricted, and the catalyst may be of any shape such as a spherical shape, a cylindrical shape, a ring shape and an amorphous shape. Of these shapes, the ring shape is more preferred since the use of such a ring-shaped catalyst has an effect of preventing heat reserve at hot spot portions. The composition and shape of the catalyst filled in an inlet portion of a reaction tube may be the same as or different from those of the catalyst filled in a lower portion thereof.

The above catalyst used in the present invention may be diluted with an inert diluting material in order to prevent formation of hot spots. The inert substance used for diluting the catalyst is not particularly restricted as long as the substances is kept stable under the reaction conditions and has no reactivity to raw materials as well as reaction products. Specific examples of the inert substance may include alumina, silicon carbide, silica, zirconium oxide, titanium oxide or the like, i.e., those usable as a carrier for catalysts. The shape of the inert substance is not particularly restricted similarly to the catalyst, and the inert substance may be of any shape such as a spherical shape, a cylindrical shape, a ring shape and an amorphous shape. The size of the inert substance may be determined in view of diameter and differential pressure of the reaction tube.

In the analysis method of the present invention, a part of the reaction production gas obtained in the production line is diverted to a branched line and then introduced into an analyzing apparatus through a double tube including an inner tube (sampling tube) and an outer tube capable of feeding a heating medium therethrough. When such a double tube is used, it is possible to solve the problems that cannot be solved by conventional sampling tubes using the electric heater or steam trace for heat retention thereof. Namely, it becomes possible to prevent temperature distribution in the sampling tube, condensation and polymerization of condensable substances which are caused when the reaction production gas is cooled to a temperature lower than a dew point thereof, clogging in the sampling tube, etc. The material of the double tube is not particularly restricted, and may be preferably made of a stainless steel.

When the linear velocity of the reaction product gas flowing through the sampling tube is too small, the sampling tube tends to be clogged. Therefore, in the present invention, the velocity of the gas flowing through the sampling tube may be controlled to usually 0.1 to 2 m/sec, preferably 0.3 to 1 m/sec.

Also, the amount of the sample required for analysis using the analyzing apparatus, especially gas chromatographic apparatus, is extremely small. For this reason, in order to increase the gas velocity flowing through the sampling tube and shorten the time required for replacing an inside of the sampling tube with the reaction product gas, an inner diameter of the sampling tube is usually 1 to 20 mm, preferably 3 to 10 mm.

As the heating medium, there may be used, for example, organic heating media such as glycerol and triethylene glycol, or inorganic heating media such as silicone oil and steam. Of these media, steam is preferably used in view of simple availability. When the heating medium is flowed through the sampling tube, the temperature distribution over the sampling tube may be reduced, so that a whole portion of the sampling tube can be kept at a temperature not less than a dew point of the reaction product gas. Meanwhile, the dew point of the reaction product gas may vary depending upon the reaction conditions, and is usually not less than 80° C., preferably not less than 120° C., more preferably not less than 150° C. for the purpose of preventing condensation of the condensable substances. Meanwhile, the term "dew point" used in the present invention means the temperature at which condensation of any substances contained in a gas such as polymerizable substances and water is recognized when the temperature of the gas is decreased. The upper limit of the dew point is not particularly restricted, and is usually not more than 30° C.

The reaction product gas may contain a trace amount of high-boiling products. The high-boiling products tend to be sometimes precipitated or crystallized in the sampling tube even when the double tube of the present invention is used as the sampling tube for temperature control thereof. However, if steam is flowed through the sampling tube at the stage where the amount of the high-boiling products precipitated or crystallized therein is still kept small, the products precipitated or crystallized in the sampling tube can be removed. Further, even though the reaction production gas is condensed and polymerized in the sampling tube by any reasons irrespective of the temperature control using the double tube, the thus produced condensates and polymers can be removed by flowing steam therethrough. Accordingly, immediately after completing the analysis of the reaction product gas introduced into the analyzing apparatus and then stopping introduction of the reaction product gas thereinto, steam is preferably flowed through the inner tube of the sampling tube from a downstream side of the sampling tube toward the reactor for cleaning the sampling tube.

Further, after the above steam cleaning and during stopping of the analysis, air or a nitrogen gas is preferably flowed through the inner tube of the sampling tube. Meanwhile, the steam, air, nitrogen gas, etc., used upon cleaning the sampling tube or during stopping of the analysis are preferably flowed in a direction reverse to the flowing direction of the substance to be sampled and analyzed, i.e., in a back-flow direction, since the effects of cleaning the sampling tube and preventing retention of the substances therein are advantageously enhanced by the reversed flow.

The analyzing apparatus used for analysis of the reaction product gas, is not particularly restricted. As such an analyzing apparatus, there may be used any preferable apparatus such as gas chromatographic apparatus and spectroscopic analyzer (using ultraviolet ray, infrared ray, near-ultraviolet ray, microwave, etc.). Of these apparatuses, the use of the gas chromatographic apparatus is preferred from the standpoints of costs and operability.

The analysis method of the present invention includes a series of operations, for example, the following steps (1) to (5) which may be automatically performed. Further, this system is applicable to automated process in which start-up and steady operations of the oxidation reactor are optimized.

(1) Reaction product gas sampling and analyzing step in which a part of the reaction product gas from the production line is supplied to a branched line, and introduced into an analyzing apparatus through a double tube that is maintained at a temperature not less than a dew point of the reaction product gas by feeding a heating medium through an outer tube thereof;

(2) Steam cleaning step in which after introducing the reaction product gas into the analyzing apparatus, the supply of the reaction product gas through the sampling tube is stopped, and then steam is flowed in the reverse direction from a downstream side of the sampling tube toward the reactor;

(3) Purge step in which after the steam cleaning but during still stopping the supply of the reaction product gas through the sampling tube, air or nitrogen is flowed in the reverse direction from a downstream side of the sampling tube;

(4) Change-over step for changing over the position from which the reaction product gas is removed (for example, changing from the front-stage reactor to the rear-stage reactor; and (5) Step of automatically repeating the above steps (1) to (4) by controlling a plurality of change-over valves using a computer.

PREFERRED EMBODIMENT OF THE PRESENT INVENTION

The present invention is described in more detail by Examples, but the Examples are only illustrative and not intended to limit the scope of the present invention.

EXAMPLE 1

According to the flow chart as shown in FIG. 2, propylene was subjected to oxidation reaction using as first reactor 10 a multipipe heat-exchange type oxidation reactor having an inner diameter of 4 m which was provided on a shell side thereof with a baffle plate for changing the flow path of a heating medium. The reactor was provided with manhole nozzle 50 (size: 24B) fitted with partition plate 52 as shown in FIG. 3, and an inside of manhole nozzle 50 was purged with a nitrogen gas supplied at a feed rate of 5 Nm$^3$/hr.

It was confirmed that the reaction product gas obtained from the reactor was a mixed gas composed mainly of 67% by weight of nitrogen and 13% by weight of acrolein.

The reaction was continued for 3 months. As a result, it was confirmed that acrolein obtained at an outlet of the reactor was free from automatic oxidation and, therefore, the operation of the reactor was stably continued.

EXAMPLE 2

The same procedure as defined in Example 1 was conducted except that the nitrogen gas as a purge gas was replaced with the waste gas discharged from the waste gas combustion apparatus through line 13 as shown in FIG. 2, thereby conducting the oxidation reaction of propylene.

The reaction was continued for 3 months. As a result, it was confirmed that acrolein obtained at an outlet of the reactor was free from automatic oxidation and, therefore, the operation of the reactor was stably continued.

COMPARATIVE EXAMPLE 1

The same procedure as defined in Example 1 was conducted except that partition plate 52 was dismounted from the manhole nozzle, and the nitrogen purge was omitted, thereby conducting the oxidation reaction of propylene.

After ten days, the outlet temperature of the reactor was rapidly increased due to automatic oxidation of acrolein. Therefore, the operation of the plant had to be stopped.

EXAMPLE 3

According to the flow chart as shown in FIG. 2, propylene was subjected to oxidation reaction using as first reactor 10 a multipipe heat-exchange type oxidation reactor having an inner diameter of 4 m which was provided on a shell side thereof with a baffle plate for changing the flow path of a heating medium. The reactor was provided with nozzles 42 (size: ¾B) for mounting a thermometer and a pressure gauge as well as manhole nozzle 50 (size: 24B) as shown in FIG. 5, and a nitrogen gas was fed to the respective nozzles 42 at a feed rate of 0.6 Nm³/hr, and to manhole nozzle 50 at a feed rate of 70 Nm³/hr.

It was confirmed that the reaction product gas obtained from the reactor was a mixed gas composed mainly of 67% by weight of nitrogen and 13% by weight of acrolein.

The reaction was continued for 3 months. As a result, it was confirmed that acrolein obtained at an outlet of the reactor was free from automatic oxidation and, therefore, the operation of the reactor was stably continued.

EXAMPLE 4

The same procedure as defined in Example 3 was conducted except that the nitrogen gas as a purge gas was replaced with the waste gas discharged from the waste gas combustion apparatus through line 13 as shown in FIG. 2, thereby conducting the oxidation reaction of propylene.

The reaction was continued for 3 months. As a result, it was confirmed that acrolein obtained at an outlet of the reactor was free from automatic oxidation and, therefore, the operation of the reactor was stably continued.

EXAMPLE 5

The reactor of the same type as used in Example 3 was filled with a catalyst for oxidation of acrolein, and used as second reactor 20 to conduct the oxidation reaction of acrolein.

Further, the reactor was provided with measuring device-mounting nozzles 42 and manhole nozzle 50 both having a double tube structure, and 200° C. steam was fed to an outer tube of the respective nozzles for heating. After these nozzles were subjected to the same nitrogen purge as in Example 3, the oxidation reaction was conducted, thereby obtaining a mixed gas composed mainly of 67% by weight of nitrogen and 13% by weight of acrylic acid.

The reaction was continued for 3 months. As a result, it was confirmed that measuring device-mounting nozzles 42 of the reactor were free from clogging and, therefore, the operation of the reactor was stably continued.

COMPARATIVE EXAMPLE 2

The same procedure as defined in Example 5 was conducted except that no nitrogen gas was fed to measuring device-mounting nozzles 42, and no steam heating was conducted. When the inside of the reactor was inspected after three months, it was confirmed that a large amount of polymers was adhered to measuring device-mounting nozzles 42.

COMPARATIVE EXAMPLE 3

The same procedure as defined in Example 3 was conducted except that no nitrogen gas was fed to measuring device-mounting nozzles 42 and manhole nozzle 50. As a result, it was confirmed that after ten days, the outlet temperature of the reactor was rapidly increased due to automatic oxidation of acrolein and, therefore, the operation of the plant had to be stopped.

EXAMPLE 6

Stainless steel reactors of a double tube structure having an inner diameter of 27 mm and a length of 5 m were used as front-stage and rear-stage reactors, and a molten alkali metal nitrate (niter) as a heating medium was fed to the respective reactors to control the reactors to a uniform temperature. The front-stage reactor was filled with 1.5 liters of a Mo—Bi—Fe-based composite oxide catalyst prepared by ordinary method, and the rear-stage reactor was filled with 1.2 liters of a Mo—V—Sb-based composite oxide catalyst prepared by ordinary method.

A mixed raw gas composed of 7 mol % of propylene, 70 mol % of air and 23 mol % of steam was flowed through the front-stage reactor at a space velocity of 1,000 hr$^{-1}$. The resultant outlet gas of the front-stage reactor was directly flowed and fed to the rear-stage reactor, thereby conducting two-stage oxidation reaction to continuously produce acrylic acid. The temperatures of the front-stage and rear-stage reactions (temperatures of the heating media fed thereto) were maintained at 330° C. and 270° C., respectively, and the temperature of a connecting portion between the front-stage and rear-stage reactors was maintained at 250° C.

A stainless steel sampling tube having an inner diameter of 3 mm was inserted into each of a front-stage reactor outlet conduit and a rear-stage reactor outlet conduit to provide a double tube having an outer diameter of 10 mm. The double tube was further connected to a gas chromatographic apparatus. The sampling tube had a length of 30 m, and 120° C. steam was fed to an outer tube side of the double tube. In addition, the outside of the double tube was covered with a 30 mm-thick heat-insulating material.

Meanwhile, the above gas chromatographic analysis system was provided with a plurality of change-over valves to automatically conduct various procedures such as change-over between portions to be analyzed, replacement, introduction and analysis of the reaction product gas, and steam cleaning and air cleaning of the sampling tube, by appropriately setting the time intervals thereof. Specifically, the procedures include the following steps (a) to (d):

(a) Step of replacing an inside of the sampling tube fitted to an outlet of the front-stage or rear-stage reactor with the reaction product gas;

(b) Step of introducing the reaction product gas into the gas chromatographic apparatus for analysis and data treatment thereof;

(c) Step of stopping the introduction of the reaction product gas and cleaning the sampling tube with steam; and (d) Step of purging the inside of the sampling tube with air.

The reactor was continuously operated for 100 days while analyzing the reaction product gas under such a condition that the time interval from analysis of an outlet gas from the front-stage reactor to that of an outlet gas from the rear-stage reactor was one hour, and the time interval from analysis of the outlet gas from the rear-stage reactor to that of the outlet gas from the front-stage reactor was two hours. As a result of the analysis of the outlet gases from the front-stage and rear-stage reactors, it was confirmed that a carbon balance thereof was maintained at 96 to 97%, i.e., no deterioration tendency of the carbon balance was observed, and further the sampling tube was free from clogging.

COMPARATIVE EXAMPLE 4

The same procedure as defined in Example 6 was conducted except that a stainless steel tube having an inner diameter of 3 mm was used as the sampling tube for reaction product gas; a steam trace through which 120° C. steam was flowed was wound around an outside of the sampling tube, and the outside of the sampling tube was further covered with a 150 mm-thick heat-insulating material; and after introducing the reaction product gas into the analyzing apparatus, etc., the sampling tube was subjected to neither steam cleaning nor air purging, thereby conducting analysis of the reaction product gas. As a result, it was confirmed that at the next day after initiation of the analysis, deterioration in the carbon balance of the outlet gas from the rear-stage reactor was commenced, and three days after initiation of the analysis, deterioration in the carbon balance of the outlet gas from the front-stage reactor was commenced. Further, it was confirmed that the rear-stage analysis line was clogged after 5 days, and the front-stage analysis line was clogged after 10 days.

COMPARATIVE EXAMPLE 5

The same procedure as defined in Comparative Example 4 was conducted except that a stainless steel tube having an inner diameter of 3 mm was used as the sampling tube for reaction product gas; an electric heater was wound around an outside of the sampling tube, and the outside of the sampling tube was further covered with a 150 mm-thick heat-insulating material; and a thermocouple was fitted at the mid portion of length of the sampling tube to control the temperature thereof to 120° C., thereby conducting analysis of the reaction product gas. As a result, it was confirmed that three days after initiation of the analysis, deterioration in the carbon balance of the outlet gas from the rear-stage reactor was commenced, and five days after initiation of the analysis, deterioration in the carbon balance of the outlet gas from the front-stage reactor was commenced. Further, it was confirmed that the rear-stage analysis line was clogged after 10 days, and the front-stage analysis line was clogged after 15 days.

INDUSTRIAL APPLICABILITY

According to the present invention, the oxidation reactor is free from local retention of the reaction gas at nozzles or manhole nozzle provided therein, so that the reaction in the oxidation reactor can be stably continued for a long period of time. Also, according to the present invention, automatic oxidation of (meth)acrolein and clogging of the nozzles or manhole nozzle due to deposition of polymers of (meth)acrolein and (meth)acrylic acid can be prevented, resulting in stable production of (meth)acrylic acid. Further, in the method for analyzing a easily-polymerizable compound according to the present invention, the reaction product gas can be prevented from being condensed and polymerized in the sampling tube. Therefore, the analysis method of the present invention is an on-line analysis method that can be conducted at a high accuracy for a long period of time, which is, therefore, highly valuable from industrial viewpoints.

What is claimed is:

1. A method for analyzing an easily-polymerizable compound by
    (a) introducing a gas containing the easily-polymerizable compound into an analyzing apparatus through a sampling tube having an inlet and an outlet connected to a reactor, wherein the sampling tube is a double tube having an inner and an outer tube, and a heating medium is fed into the outer tube of the sampling tube;
    (b) analyzing the gas in the inner tube of the sampling apparatus;
    (c) after completing the analysis of step (b) stopping the introduction of gas into the inner tube of the sampling apparatus;
    (d) cleaning the sampling tube by flowing stream through the inner tube of the sampling tube from a downstream side of the sampling tube toward the reactor, and after the cleaning of step (c) and while analysis is stopped; and
    (e) flowing air or nitrogen gas through the inner tube of the sampling tube in a reverse direction of the gas sampled and analyzed.

2. A method according to claim 1, wherein the gas containing the easily-polymerizable compound is a reaction gas obtained by subjecting propane, propylene or isobutylene to catalytic gas-phase oxidation reaction.

3. A method according to claim 1, wherein the gas containing the easily-polymerizable compound is maintained at a temperature not less than a dew point thereof.

4. A method according to claim 1, wherein after completion of the analysis, the sampling tube is cleaned by flowing steam through an inner tube thereof.

* * * * *